US006291228B1

(12) United States Patent
Howard et al.

(10) Patent No.: US 6,291,228 B1
(45) Date of Patent: *Sep. 18, 2001

(54) VACCINE

(75) Inventors: John Christopher Howard; Michael Cyril Clarke; John Brownlie, all of Compton (GB)

(73) Assignee: Vericore Limited, Leyland (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/605,274

(22) Filed: Feb. 7, 1996

Related U.S. Application Data

(62) Continuation of application No. 08/416,452, filed on Apr. 3, 1995, now abandoned, which is a continuation of application No. 08/279,272, filed on Jul. 22, 1994, now abandoned, which is a continuation of application No. 08/146,829, filed on Oct. 29, 1993, now abandoned, which is a continuation of application No. 07/998,777, filed on Dec. 24, 1992, now abandoned, which is a continuation of application No. 07/634,197, filed as application No. PCT/GB89/00882 on Aug. 3, 1989, now abandoned.

(30) Foreign Application Priority Data

Aug. 3, 1988 (GB) .................................................. 8818415

(51) Int. Cl.$^7$ ........................................................ C12N 7/04
(52) U.S. Cl. .......................... 435/236; 435/325; 435/237; 424/218.1
(58) Field of Search ................................ 424/218.1, 93.1, 424/93.2, 93.6, 813; 435/235.1, 236, 237, 325

(56) References Cited

U.S. PATENT DOCUMENTS

| | | |
|---|---|---|
| 3,122,477 | 2/1964 | Beckenhauer et al. . |
| 3,293,129 | 12/1966 | Baker . |
| 3,346,456 | 10/1967 | Baker . |
| 3,577,525 | 5/1971 | Baker . |
| 3,838,004 | 9/1974 | Mebus et al. . |
| 3,839,556 * | 10/1974 | Mebus ................................ 424/89 |
| 3,869,547 * | 3/1975 | Mebus ................................ 424/89 |
| 3,873,422 | 3/1975 | Mebus . |
| 3,914,408 | 10/1975 | Mebus . |
| 3,919,044 | 11/1975 | Melnick et al. . |
| 3,919,412 | 11/1975 | Mebus . |
| 3,919,413 | 11/1975 | Mebus . |
| 3,925,544 | 12/1975 | Shechmeister et al. . |
| 4,618,493 * | 10/1986 | Delgoffe ............................. 424/89 |
| 4,714,678 * | 12/1987 | Delgoffe ........................... 435/235 |
| 4,806,370 | 2/1989 | Gerber . |
| 4,900,549 | 2/1990 | De Vries et al. . |

FOREIGN PATENT DOCUMENTS

| | | | |
|---|---|---|---|
| 0106831 | 4/1984 | (EP) . | |
| 0109942 * | 5/1984 | (EP) | ............................. A61K/39/00 |
| 0 208 507 A2 | 1/1987 | (EP) . | |
| 0 231 039 B1 | 8/1987 | (EP) . | |
| 0 436 620 B1 | 7/1991 | (EP) . | |
| 992330 | 5/1965 | (GB) . | |
| 1023526 | 3/1966 | (GB) . | |
| 1402565 | 7/1975 | (GB) . | |
| 1560344 | 2/1980 | (GB) . | |
| 2079786 | 2/1982 | (GB) . | |

OTHER PUBLICATIONS

Vaccination–challenge Experiments Table, 1 sheet.

"Vaccination Helps Cut Fertility Costs," *Dairy Farmer*, Jul. 1, 1998, 1 sheet.

"Bovidec® Controlling BVD Infertility," C–Vet, 3 sheets.

"Triangle 1—Bovine Virus Diarrhea Vaccine," Fort Dodge, 2 sheets.

"Bovine Viral Diarrhoea," *OIE Manual*, 1996, Chapter X.5. Not In the Code, pp. 651–659.

Bates, Andrew, "Light at the End of the Tunnel," *BCVA Congress Times*, Apr. 22, 1998, pp. 1–2.

Brownlie, Joe, "Clinical Aspects of the Bovine Virus Diarrhoea/Mucosal Disease Complex in Cattle," *In Practice*, Nov. 1995, pp. 195–202.

Brownlie, Joe, "The Pathways for Bovine Virus Diarrhoea Virus Biotypes in the Pathogenesis of Disease," *Arch Virol*, 1991, Suppl. 3, pp. 79–96.

Brownlie, J. et al., "Experimental Infection of Cattle in Early Pregnancy with a Cytopathic Strain of Bovine Virus Diarrhoea Virus," *Research in Veterinary Science*, 1989, 46, pp. 307–311.

Brownlie, J. et al., "Pathogenesis and Epidemiology of bovine Virus Diarrhoea Virus Infection of Cattle," *Ann Rech Vet*, 1987, 18, pp. 157–166.

Brownlie, J. et al., "Protection of the Bovine Fetus from Bovine Viral Diarrhoea Virus by Means of a New Inactivated Vaccine, '*The Veterinary Record*, Jul. 15, 1995, pp. 58–63.

Brownlie, J. et al., "Scientific Reports: Cattle—Mucosal Disease," Annual Report of the Institute for Animal Health, 1987, p. 20.

Corapi, Wayne V. et al., "Monoclonal Antibody Analysis of Cytopathic and Noncytopathic Viruses from Fatal Bovine Viral Diarrhea Virus Infections," Journal of Virology, Aug. 1998, pp. 2823–2827.

(List continued on next page.)

Primary Examiner—Laurie Scheiner
(74) Attorney, Agent, or Firm—Crompton, Seager & Tufte, LLC

(57) ABSTRACT

A vaccine comprises a non-cytopathogenic strain of bovine viral diarrhoea virus, grown in a bovine derived cell line such as MDBK and killed, for example with β-propiolactone. The adjuvant is Quil A.

3 Claims, No Drawings

OTHER PUBLICATIONS

Dalsgaard, Kristian et al., "classical and new Approaches to Adjuvant Use in Domestic Food Animals," *Advances in Veterinary Science and Comparative Medicine*, (1990) vol. 35, pp. 121–160.

Harkness, J.W. et al., "The Efficacy of an Experimental Inactivated BVD–MD Vaccine," Commision of the European Communities Seminar, Sep. 1985, pp. 233–251.

McClurkin, A. W. et al., "Evaluation of Acetylethyleneimine–killed Bovine Viral Diarrhea—Mucosal Disease Virus (BVD) Vaccine for Prevention of BVD Infection of the Fetus," *Proc. U.S. Animal Health Assoc.*, (1975) 79, pp. 114–123.

Stewart–Tull, Duncan et al., "Use of Mineral Hydrocarbons in Human and Veterinary Vaccines," date unknown, 11 sheets.

Stott, E.J. et al., "Preliminary Observations on 'Quil–A' as an Adjuvant for an Inactivated Respiratory Syncytial Virus Vaccine," *Report and Proceedings from the Symposium on Vaccine Adjuvants held in London on the 30$^{th}$ March, 1981*, Nov. 1981, pp. 19–24.

Barie, S. et al., Comparison of the Potency for Cattle of Trivalent FMD Caccines Adjuvanted by Aluminum Hydroxide–Saponin or Oil Emulsion, *Zbl. Vet. Med. B*, 26, 464–460 (1979).

Stott, E.J. et al., Development of a Potent Inactivated Vaccine Against Respiratory Syncytial Virus Infection of Calves, *Proceeding of the 14 World Congress on Diseases of Cattle*, pp 669–674 (1986).

Morgan, D.O., et al. Vaccination Against Foot–and–Mouth Disease, *New Developments with Human and Veterinary Vaccines*, pp 169–178 (1980).

Sutmoeller, P. et al., *The FMD Vaccine Situation in South America*, pp 304–321.

Bittle, J.L., et al., Carriers and Adjuvants for Chemically Synthezied Antigens, *Advances in Carriers and Adjuvants for Veterinary Biologics*, pp 151–156 (1986).

Holly J. Neaton, *Veterinary Medicine*, 81 (1986) 876–881.

S.P. Morzaria, *The Veterinary Record*, Nov. 3, 1979, 410–414.

B. Morein, et al. *Veterinary Immunology and Immunopathology*, 17 153–159.

*Livestock Farming*, (1987), 25, 30.

A.W. McClurkin and M.F. Coria, *Archives of Virology*, (1978), 58, 119–125.

Kristian Dalsgaard, *Archiv fur die gesamte Virus forschung*, (1974), 44, 243–254.

K. Dalsgaard and E. Overby, *Acta vet. Scand.* (1976) 17, 465–474.

Tsretkov, et al. *Vet Med. Nauki* (1979) 16, 3–9. Abstract only.

P. Zwetkow, et al. from the Veterinary Institute of Immunology Sofia.

Comment from the *The Veterinary Record* 114, Jun. 22, 1984.

Brownlie, et al. *The Veterinary Record* Jun. 2, 1984, 535–536.

M. Eskildsen and E. Overby *Acta Vet. Scand.* (1976) 17, 131–141.

Meyling et al. EC seminar on pestivirus infection of ruminants.

Stott, et al. *Proceedings of the 14 World Congress on Diseases of Cattle*, (1986) pp. 669–674.

Fernelius et al. *Am J. Vet. Res.* (1972) 33, 1421–1431.

\* cited by examiner

VACCINE

This is a continuation of application(s) Ser. No. 08/416,452 filed on Apr. 3, 1995, now abandoned which is a continuation of Ser. No. 08/279,272 filed on Jul. 22, 1994, now abandoned which is a continuation of Ser. No. 08/146,829 filed on Oct. 29, 1993 now abandoned which is a continuation of Ser. No. 07/998,777 filed on Dec. 24, 1992, now abandoned, which is a continuation of Ser. No. 07/634,197, filed on Jan. 17, 1991, now abandoned, which is a 371 of PCT/GB89/00882 filed Aug. 3, 1989.

Bovine virus diarrboea virus (BVDV) is extremely common in cattle in the UK, the remainder of Western Europe, North America, Australia and Africa. Infection with this virus may result in a variety of syndromes and pathologies influenced largely by the age of animals when first infected. In young, previously uninfected calves the virus causes a transient infection. This is associated with leucopenia, and an interrelated period of immunosuppression and increased susceptibility to infection with other microorganisms. BVDV is, after RSV (respiratory syncitial virus), probably the most important virus associated with outbreaks of respiratory disease in young housed calves and because of its immuno-suppressive effect it may be involved in other calf infections, for example enteritis. This virus is also considered to be a major contributor to disease in "feedlot calves" in the USA and Canada. Following recovery, animals exhibit a degree of immunity to reinfection. However, this immunity appears not to be absolute or lifelong.

More serious problems result from infection of pregnant cattle. Abortion may ensue or alternatively deformities may be produced in the foetus that is carried to term; these deformities may result from exposure to virus at the time when immunocompetence is developing and could be the result of an incomplete immune response. Infection of the foetus before immunocompetence develops can result in the foetus remaining viraemic through the period of gestation and the subsequent birth of a calf that remains persistently viraemic, with a non-cytopathogenic form of the virus, and specifically immunotolerant to BVDV for life. Such calves are the animals that die later of mucosal disease; an event triggered by superinfection with a cytopathogenic variant of BVDV.

It has been estimated that about 0.4% of apparently normal beef calves in the UK are viraemic and these animals represent a major source of infection on farms.

Traditionally, viral vaccines fall into two classes: live vaccines containing live viruses which have been treated or grown (attenuated) in such a way as to make them less pathogenic, and vaccines containing killed (inactivated) virus particles. In the context of BVDV, the viruses themselves may be cytopathogenic or non-cytopathogenic. Thus, in principle, four main classes of BVDV vaccine could exist, although the vast majority of commercial vaccines are based on the cytopathogenic virus. Moreover, it is thought by many that live vaccines are unacceptable because live cytopathogenic vaccine strains may produce death from mucosal disease in persistently viraemic animals, and live non-cytopathogenic virus vaccine may infect the foetus in pregnant cattle and result in any of the diseases outlined above.

Infection via the respiratory tract is probably the most important route of transmission of the virus on farms and protection against spread via this route would be expected to have a major beneficial effect in controlling disease due to BVDV.

Parenteral vaccination with inactivated BVDV protected against respiratory infection. In one experiment all of 5 vaccinated calves were resistant to respiratory challenge and all of 5 controls became infected.

The killed BVDV antigens tested induced the production of high titres of neutralising antibodies. These were shown to rise from less than 50 before vaccination to greater than or equal to 2,000–10,000 units after vaccination.

The present invention provides a vaccine comprising a killed, non-cytopathogenic virus, wherein the virus is grown on a cell line which is derived from bovine cells such as the MDBK cell line (Madin Darby Bovine Kidney; Madin & Darby (1958); available from ECACC, Salisbury, Wiltshire, UK) and is adjuvanted with Quil A. MDBK cells are available in many laboratories throughout the world. Other bovine cell lines useful in the practice of the invention include EBL cells, NM5 cells, LWC874 cells and CTe cells.

The MDBK cell line is preferably used at passage levels 147–187, more preferably at pass 147 to 157 and most preferably at pass 147. Seed virus is preferably prepared by adding about $10^6$ $TCD_{50}$ of BVDV (non-cytopathogenic strain) to confluent cultures of calf testis cells. Calf testis cells are preferred to grow the seed culture because virus yields are higher in these cells, whereas yields of antigen are greater in MDBK cells. The cells may be grown in roller bottles with Eagle's MEM medium and added foetal bovine serum 7.5%, sodium bicarbonate 0.11% and lactalbumin hydrolysate 0.25%. After addition of the virus, the culture may be maintained with 50 ml medium; Eagle's BME with foetal bovine serum 2%, sodium bicarbonate 0.17%, lactalbumin hydrolysate 0.25% and magnesium chloride hexahydrate 0.6%. The culture may be incubated at about 36° C. for 5 to 9 days, preferably 7 days, and then subjected to a single cycle of freeze/thaw. The suspension may be centrifuged at about 500 g for 4 to 6 minutes, preferably 5 minutes, to remove gross debris and the supernatant fluid stored in small volumes, ready for use, at about −70° C. The titre of the stored seed virus may be determined by assay in cultures of calf testis cells.

Virus antigen is prepared by adding about 1 ml of seed virus, containing about $10^6$ $TCD_{50}$ of BVDV, to cultures of MDBK cells. These cells may be grown in roller bottles with Eagle's REM, foetal bovine serum 10% and sodium bicarbonate 0.11% and are used after about 4 days' growth when the cultures are about 75% confluent. After addition of the virus the culture may be maintained with 125 ml of BME medium (vide supra). Seven days later when the culture contains about $10^8$ cells and a virus titre of about $10^{8-5}$ $TCD_{50}$, β-propiolactone is added to a concentration of 1 in 500 and the bottle rolled for 3 hours at 36° C. to inactivate the virus. Complete inactivation of the antigen preparation is checked by passage of samples in cultures of calf testis cells. The antigen is stored at −20° C.

Before cell cultures are used for the preparation of seed virus and virus antigen they are checked for the presence of adventitious BVDV. Foetal bovine serum is checked for freedom from virus and BVDV antibody.

One dose of the vaccine is prepared by mixing 1 mg of "Quil A" (Superfos A/S, Denmark) as 50 ul of a stock (20 mg/ml in water) to 4 ml of beta-propiolactone-inactivated virus. This is injected subcutaneously behind the shoulder of calves, aged about 3 months and shown to be free of BVDV antibody, either maternally derived or produced as a result of infection.

Vaccinated calves showed an antibody response (Table 1), determined by ELISA (Howard, Clarke & Brownlie, 1985), which was detected 6 weeks after the first vaccination. These animals and unvaccinated controls were challenged with a strain of BVDV (11249nc) selected because of its tropism for the respiratory tract and consistent rate of naso-pharyngeal shedding. Calves were infected intranasally on week 8. Virus shedding was determined by examination of naso-pharyngeal swabs (blood was also tested) for up to 10 days after challenge and samples were assayed in cultures of calf testis cells. BVDV was recovered from the control animals (Tables 2,3) but not the vaccinated group. The relationship, for individual animals, between antibody levels at the time of challenge and the susceptibility to infection is shown in Table 3. None of the controls had detectable antibody at the time of challenge and their all became infected and seroconverted (Table 1).

BVDV antigen may be included with other microorganisms (preferably inactivated) to form a multivalent vaccine. Suitable organisms include respiratory syncytial virus, parainfluenza 3 virus and *Mycoplasma bovis*.

Instead of using whole virus, it may be advantageous to separate the antigens from the virus and to use them with Quil A and, optionally, suitable carriers and the like. This may be achieved by known means.

TABLE 1

Antibody responses by ELISA[1] in calves vaccinated with strain Ky1203nc

| Group | No. of Calves | week[2] | | | | | |
|---|---|---|---|---|---|---|---|
| | | 0 | 3 | 6 | 8 | 10 | 12 |
| Non-vaccinated | 5 | 1.4 | ND | ND | 1.4 | 2.09 +0.60 | 2.50 +0.12 |
| Vaccine standard dose | 5 | 1.4 | 1.4 | 3.07 +0.30 | 3.52 +0.13 | 4.38 +0.25 | 4.09 +0.29 |

[1]mean number of units of antibody ($10^n$) ± SD
[2]calves vaccinated on weeks 0, 3 and 6; challenged on week 8 with strain 11249nc intransally.

TABLE 2

Effect of vaccination with strain Ky1203nc on infection with BVDV

| Group | No. of Calves | No. of calves infected[1] on indicated day | | | | |
|---|---|---|---|---|---|---|
| | | 0 | 4 | 6 | 8 | 10 |
| Non-vaccinated | 5 | 0 | 1 | 5 | 1 | 0 |
| Vaccine-standard dose | 5 | 0 | 0 | 0 | 0 | 0 |

[1]Isolations from nasopharyngeal swabs

TABLE 3

Relationship between antibody at time of challenge and susceptibility to infection in individual animals

| Animal Code No. | Vaccine[1] | Antibody[2] | Virus isolation[3] | | Leucopenia %[4] |
|---|---|---|---|---|---|
| | | | N. Ph. swab | Blood | |
| X502 | S | 3.71 | − | − | 5 |
| A21 | S | 3.57 | − | − | 0 |
| X694 | S | 3.51 | − | − | 0 |
| X657 | S | 3.42 | − | − | 0 |
| X684 | S | 3.38 | − | − | 5 |
| A10 | − | 1.4 | + | − | 46 |
| A407 | − | 1.4 | + | + | 48 |
| X192 | − | 1.4 | + | + | 53 |
| X658 | − | 1.4 | + | + | 52 |
| X659 | − | 1.4 | + | + | 54 |

[1]Animals given standard dose (S), or no vaccine (−)
[2]Units of antibody ($10^n$) by ELISA on day of challenge, animals arranged in decreasing order
[3]Isolations from nasopharyngeal swab as in Table 2, isolations from blood on day 6
[4]Percentage reduction in cell count, compared to average of 3 preinoculation values The MDBK (Madin-Darby Bovine Kidney) cell line has been available for about 25 years from the American Type Culture Collection, Manassas, Va., USA as ATCC CCL 22. Since 1982, this line has been BVD-free. The same cell line has also been available from the European Collection of Animal Cell Cultures, Porton Down, Salisbury, Wiltshire, UK, as has MDBK from another source, under the accession number ECACC No. 85102401. A sample of the latter deposit has now been deposited with ECACC under the Budapest Treaty, with the date of 2nd Aug. 1989 and the accession number 89080201.

We claim:

1. A process for preparing a vaccine comprising the steps of
   (a) inoculating a cell line derived from bovine cells selected from the group consisting of MDBK, EBL, NM5, LWC874 and CTe cells with a non-cytopathogenic bovine viral diarrhoea virus (BVDV);
   (b) growing said virus in the inoculated cells;
   (c) inactivating virus from step (b); and
   (d) admixing material from step (c) with Quil A.

2. A process according to claim 1 wherein the cell line comprises MDBK cells.

3. A process according to claim 1 wherein the inoculum with which said cell line is inoculated comprises BVDV grown in calf testis cells.

\* \* \* \* \*